United States Patent [19]

Dunbar, IV

[11] Patent Number: 4,708,139
[45] Date of Patent: Nov. 24, 1987

[54] ARTHROSCOPIC DRILL GUIDE

[76] Inventor: William H. Dunbar, IV, 536 E. Arrellaga St., Santa Barbara, Calif. 93103

[21] Appl. No.: 832,402

[22] Filed: Feb. 24, 1986

[51] Int. Cl.⁴ ............................................. A61F 17/32
[52] U.S. Cl. ............................... 128/305.1; 128/310; 408/115 R
[58] Field of Search ................. 128/303 B, 348.1, 346, 128/310, 305.3, 92 EB, 92 E, 92 EA, 92 EC, 305.1; 408/72 R, 72 B, 103, 115 R, 115 B, 241 G

[56] References Cited

U.S. PATENT DOCUMENTS

| | | | |
|---|---|---|---|
| 3,049,018 | 8/1962 | Lusskin et al. | 128/310 |
| 4,312,337 | 1/1982 | Donohue | 128/310 |
| 4,535,768 | 8/1985 | Hourahane et al. | 128/305.1 |

FOREIGN PATENT DOCUMENTS

| | | | |
|---|---|---|---|
| 153831 | 9/1985 | European Pat. Off. | 128/310 |
| 445426 | 5/1975 | U.S.S.R. | 128/305.1 |

OTHER PUBLICATIONS

Stryker Nisonson Wire and Drill Guide System, Jul. 1984.
Acufex Arthroscopic ACL Drill System, 1984.
Synthes Combined Aiming Device, 1981.
Richards Arthroscopic Ligament Drill Guide, 1984.
Dyonics Vector Guide to the Knee System, 1985.
Arthrex Variable Radius-VR Drill Guide System.

Primary Examiner—Z. R. Bilinsky
Attorney, Agent, or Firm—Sherman and Shalloway

[57] ABSTRACT

An improved arthroscopic drill guide is disclosed herein including a frame having a probe fixedly mounted thereto. A slide member is slidably and adjustably mounted to an end of the frame remote from the end to which the probe is fixedly mounted. The slide member features a locking mechanism that enables the frame and slide assemblies to be fixed one to the other. The slide, at an end distal from its slidable mounting to the frame, has a guide portion into which is slidably mounted a cannula which is aligned with a tip portion of the probe. The cannula comprises a drill guide through which the drill bit is reciprocated so as to enable the drilling of holes for the purpose of ligament installation. The probe is specifically shaped so as to render the drill guide usable for the drilling of the femoral and tibial holes without the necessity of providing a separate probe for each hole which is to be drilled.

12 Claims, 7 Drawing Figures

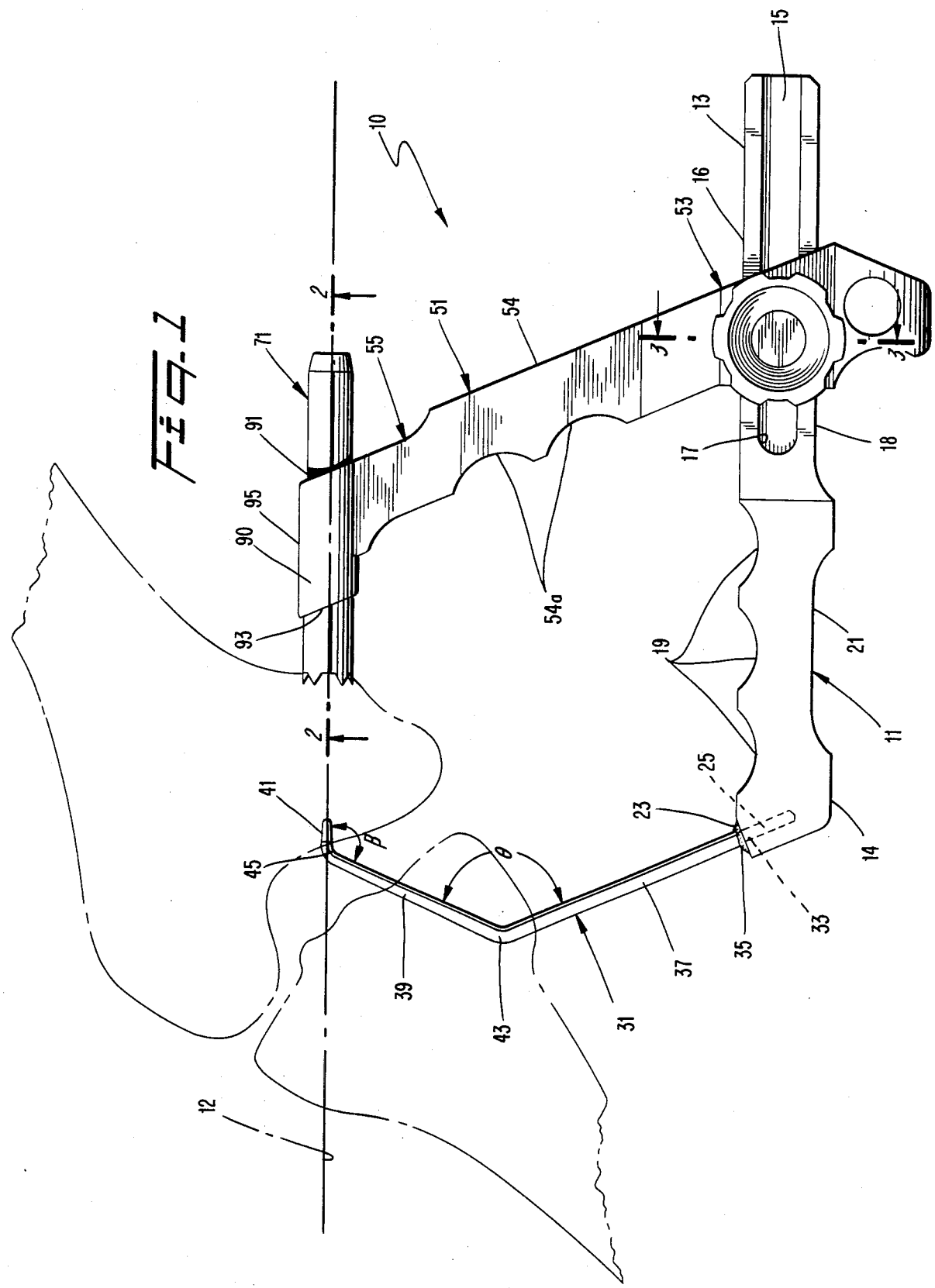

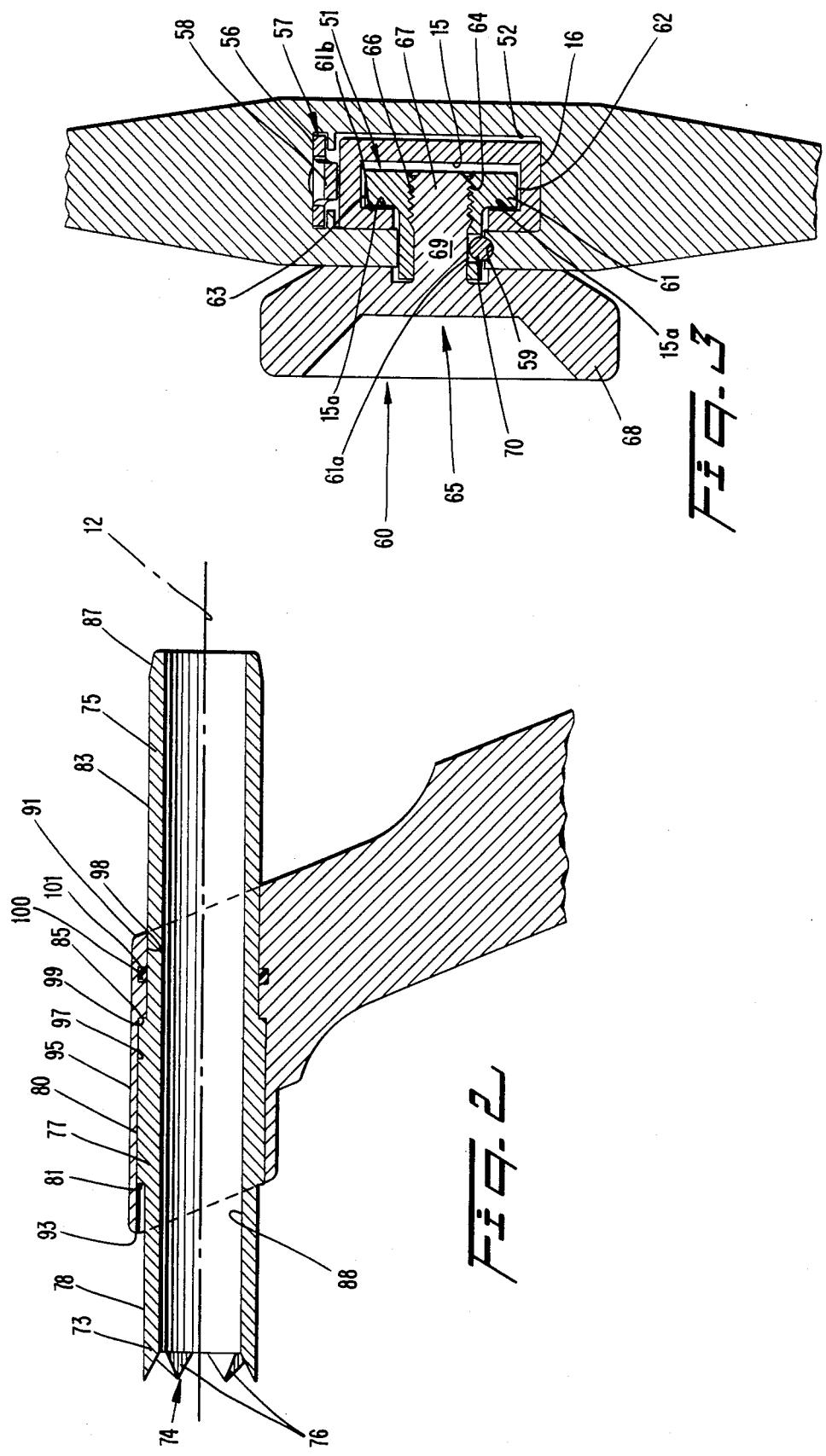

ARTHROSCOPIC DRILL GUIDE

BACKGROUND OF THE INVENTION

The present invention relates to an improved arthroscopic drill guide. Arthroscopic drill guides known in the art typically have the drawback of requiring a separate probe for each drilling procedure. This occurs since each known probe is not adaptable to the different possible physical arrangements of the holes to be drilled in the respective bones.

Further, prior art drill guides are in many cases cumbersome and complicated to use and do not have a simple means incorporated therewith to adjust the distance between the probe and the drill bit guiding structure itself. In a further aspect, most prior art drill guides have not been designed so as to coaxially align the probe tip with the drill bit guiding structure and because of this, such instruments are difficult to utilize with the required accuracy. In those instruments which do align the probe tip with the drill guiding structure, the drill guide structure is not manufactured to a sufficiently precise tolerance so as to benefit from the advantages which are provided through such alignment.

The following prior art is known to Applicants:

Richards Medical Company has disclosed an arthroscopic ligament drill guide including a hook/probe which is separately engaged to the bone and thereafter connected to an assembled handle/drill guide arm. When so assembled, the drill guide arm is tapped into position on the bone and thereafter a drill is inserted therethrough to perform the drilling operation. The requirements of the installation of the handle and drill guide arm about the probe in situ makes this device extremely cumbersome to use in light of its design. Further, when so assembled, the drill guide is at substantially a right angle to the probe, leading to inherent inaccuracies in the location of the proposed tunnel. Further, the Richards device includes an extremely short clamping region which clamps the drill guide arm to the handle. This arrangement, together with the remoteness of the clamping region from the region of the proposed tunnel, causes magnification of inaccuracies in alignment of the drill guidearm with respect to the probe.

Dyonics, Inc. has disclosed a drill guide with the trademark name "Vector." The "Vector" device includes a probe fixedly mounted on a first arcuate arm which is in turn, pivotably mounted on a second arcuate arm. This second arm carries a drill guide which is slidable and adjustable therealong. The design of the "Vector" guide is such that the probe tip is never axially aligned with the drill guide portion. Furthermore, the pivotal relationship between the frame members which respectively carry the probe and the drill guide gives rise to inherent instabilities during the use of the device. This occurs since there is no way to ensure that the probe tip and drill guide portion lie in a common plane; the co-planar arrangement being one optimum way of ensuring the proper alignment of the instruments for accurate drilling.

Arthrex Arthroscopic Instruments, Inc. has disclosed a drill guide system identified with the trademark "Variable Radius." This device utilizes a structure which is described as having a "bow and arrow" design whereby an arcuate frame has the probe tip adjustably mounted therein in an elongated arcuate slot and the drill guide portion is reciprocable at one end of the arcuate frame. While this structure ensures that the probe tip and the drill guide portion will lie in a common plane, the extent of the arcuate portion of the frame precludes the probe tip and the drill guide portion from ever being coaxial, thereby causing a loss of the inherent accuracy which might otherwise be attainable through the use of the device.

Stryker, Incorporated has disclosed a drill guide system identified by the name "Nisonson" which system includes a curved probe having a probe tip extending in what appears to be axial alignment with a drill guide mounted thereto. The Nisonson system does not include any means to lock the position of the drill guide portion with respect to the probe tip and thus its effectiveness as a surgical tool appears to be limited, at least in this respect.

Acufex Microsurgical, Inc. has disclosed an arthroscopic drill system including a probe tip which curves around to be in axial alignment with a drill guide portion slidably and adjustably mounted with respect to the frame. The frame carries the probe and probe tip. While this structure is at least generally related to the teachings of the present invention, it does not take into account the anatomical considerations necessary to provide an easily adjustable and versatile device which is adaptable to drilling of the tunnels in both the tibia and femur. The Acufex system incorporate a different probe for each of the two tunnels that are drilled. In addition, the probes are far too flexible to maintain proper alignment with the guide portion, thus inherently permitting drilling errors.

The Robert Mathys Company has disclosed a drill guiding system under the trademark name "Synthes" which includes interchangeable probes and probe tips some of which suggest alignment with the drill guide portion and some of which are substantially perpendicular thereto. The necessity for a plurality of interchangeable probes and probe tips renders the Synthes system cumbersome and difficult to manage during the surgical procedure due to the necessity of disassembling and reassembling the instrument for each particular ligament tunnel.

SUMMARY OF THE INVENTION

The present invention overcomes the deficiencies inherent in prior art drill guiding systems and provides a drill guiding system which allows the surgeon to drill ligament tunnels in both the femur and tibia without the need for tedious and time consuming disassembly and reassembly of instruments in situ. The present invention also includes sufficient accuracy in its construction and operation so as to enable the surgeon to drill ligament tunnels with great precision to within 1 millimeter accuracy. The present invention includes the following interrelated features:

(a) A frame is provided having a probe mounted at one end, the probe having a unique bend configuration so as to facilitate accessibility to the anatomical points of origin of proposed ligament tunnels at both the femur and tibia.

(b) The frame has located at its end remote from the end to which the probe is mounted, a means for slidably mounting a slide member and positioning the slide member at any location deemed necessary for drilling in bone.

(c) The slide member features a rectangular through hole into which the frame fits and a locking mechanism which serves to secure the slide and frame members together once they are positioned correctly.

(d) The slide has, at its end remote from the end with which it is slidably attached to the frame, a guide device with a hole therethrough.

(e) A cannula is slidably mounted through the hole of the guide device. The cannula includes a bore which enables a drill bit to be reciprocated therethrough during the drilling operation.

(f) The probe includes a probe tip which is bent so as to be coaxial with the cannula. The cannula also includes a multi-toothed face configuration facing the probe tip in axial alignment therewith. The multi-toothed face configuration is provided so as to enable the cannula to bite into the bone regardless of cannula orientation. The cross-sectional shape of the probe is designed to bias any flexing the probe will experience in use when the system is placed under tension at opposite sides of either bone. The result is a limited "opening up" of the probe only within the original plane of the system—a movement which precludes any significant misalignment.

(g) The slidable position of the slide with respect to the frame may be adjusted quite easily in situ so that the spacing between the probe tip and the multi-toothed face configuration of the cannula may be adapted to bones of differing configurations and sizes.

(h) The frame and slide each have recesses therein which facilitate their being gripped by the surgeon so as to facilitate the accurate placement of the drill guide at its location of use.

(i) In a further aspect, the axial alignment of the probe tip with the cannula facilitates error free drilling. In fact, drilling accuracy resulting from the use of the present invention eliminates the need for a Kirschner wire and hollow drill bit in drilling appropriate holes, which instruments are necessary to ensure accuracy in prior art devices.

Accordingly, it is a first object of the present invention to provide an improved arthroscopic drill guide.

It is a further object of the present invention to provide an improved arthroscopic drill guide which may be used to drill ligament tunnels in both the femur and tibia without time consuming exchanges of component parts.

It is a still further object of the present invention to provide such an improved arthroscopic drill guide which facilitates great accuracy in drilling by providing precise axial alignment of the probe tip and cannula/drill guiding member thereof.

It is a still further object of the present invention to provide such an improved arthroscopic drill guide with ease of adjustability of the cannula/drill-guiding member with respect to the probe tip in the axial direction.

It is still a further object of the present invention to provide such an improved arthroscopic drill guide which can be locked in place on the bone in order to free the surgeon's hands to prepare for and carry out the drilling itself.

These and other objects, aspects and features of the present invention will be better understood from the following description of the preferred embodiments when read in conjunction with the appended drawing figures.

BRIEF DESCRIPTION OF THE DRAWINGS

FIG. 1 shows a side view of the preferred embodiment of the present invention.

FIG. 2 shows a cross-sectional view of a portion of FIG. 1 rotated 90° with respect to the line 2—2 of FIG. 1.

FIG. 3 shows a further cross-sectional view along the line 3—3 of FIG. 1.

DESCRIPTION OF THE PREFERRED EMBODIMENT

Figure 4:
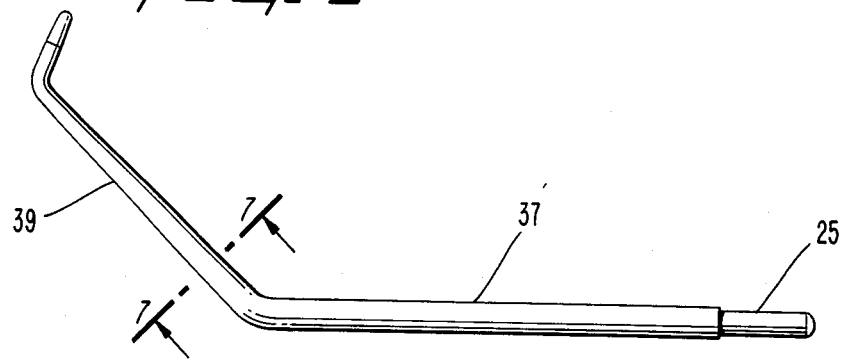
FIG. 4 shows a side view of the inventive probe.

Referring first to FIG. 1, the improved arthroscopic drill guide 10 is seen to include a frame 11, a probe 31, a slide 51 and a cannula 71.

With reference to FIGS. 1 and 3, the frame 11 is seen to include a first end 13 and a second end 14. The first end 13 includes a groove 15 best seen in FIG. 3 to be of a C-shaped cross-section. This groove 15 terminates at 17 in a preferably radiused termination point. The second end 14 of the frame 11 includes recesses 19 provided for the fingers of the surgeon and a recess 21 which enables the thumb of the surgeon to be comfortably supported thereby. Thus, the second end 14 of the frame includes the structure facilitating the grasping of the frame by the surgeon during the use of the drill guide 10.

The second end 14 of the frame 11 includes an oblique face 23 having a short hole 25 therein. As best seen in FIG. 1, the probe 31 includes a small diameter end 33 which is insertable into the hole 25 so as to mount the probe 31 to the frame 11. Since the inventive drill guide is specifically designed so as to be usable to drill the ligament tunnels in both the tibia and femur, the probe 31 may be permanently attached to the frame 11 through the use of, for example, silver solder as depicted by reference numeral 35.

With further reference to FIGS. 1 and 4–7, the probe, besides the small diameter section 25 is seen to be comprised of three sections, a first section 37, a second section 39, and the probe tip 41. The first section 37 extends substantially perpendicular to the oblique face 23 of the frame 11, until its intersection with the second section 39 at the bend 43. The bend 43 is crucial because it allows the probe 31 via the interaction between the cannula 71 and the probe tip 41 to access the anatomical point of origin of the ligament tunnels for both the femur and tibia. In the preferred embodiment, the angle $\theta$ subtended between the first section 37 and the second section 39 is approximately 135°.

The second section 39 connects the first section 37 with the probe tip 41. As shown in particular in FIG. 5, the cross-section of the first section 37 consists of top and bottom flat sides 34 and 36 connected together by arcuate side portions 38 and 40. The cross-section of the second section 39 is seen in FIG. 7 and is similar to the cross-section of the first section 37, however, as may be seen from a comparison of FIGS. 5 and 7, the second section 39 adjacent the bend 43 is wider than the width thereof adjacent the bend 45 defining the beginning of the probe tip 41.

Figure 7:
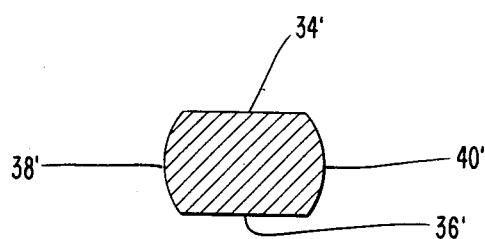
FIG. 7 shows a cross-sectional view along the line 7—7 of FIG. 4.

As shown in FIG. 7, the cross-section of the second section 39 is defined by top and bottom sides 34' and 36' and side portions 38' and 40'. The sides 34', 36', 38' and 40', respectively, are merely continuations of the above-described sides 34, 36, 38 and 40 defining the first section 37. As should be understood from FIG. 5, the sides 38' and 40' of the second section 39 taper toward one another from the bend 43 to the bend 45.

Figure 5:
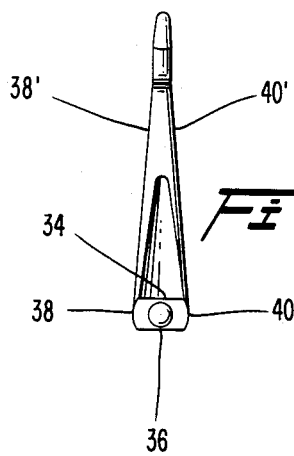
FIG. 5 shows an end view of the probe shown in FIG. 4.

Viewing the second section 39 from the perspective of FIGS. 5 and 7, it is important to understand that the combination of the taper of the second section 39 and its flat lateral configuration in the direction of the sides 38' and 40' causes the second section 39 to resist lateral movements thereof in a far superior way than would a cross-section of circular configuration. This aspect of the second section 39 in conjunction with the flat lateral configuration of the first section 37, as best seen in FIG. 5, causes the probe 31 to resist lateral forces which would tend to misalign the probe 41 with respect to the cannula 71. These features increase the reliability and accuracy of the drill guide 10 and render it far superior to all known prior art drill guides.

Figure 6:
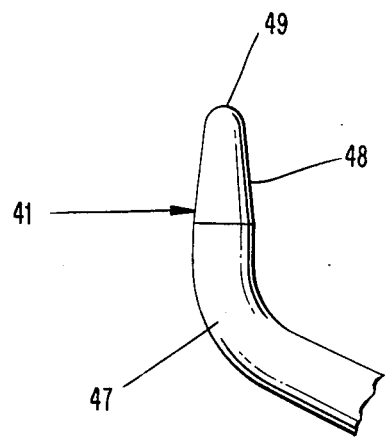
FIG. 6 shows an enlarged side view of the tip of the probe shown in FIG. 4.

With reference now to FIGS. 1, 4 and 6 in particular, it is seen that the probe tip 41 includes a proximal portion 47, preferably of circular cross-section, a distal portion 48 also preferably of circular cross-section, and a terminus 49 preferably comprising a portion of the surface of a sphere. As may be seen in FIG. 6, the proximal portion 47 is substantially cylindrical in configuration whereas the distal portion 48 consists of a conical entity. In the preferred embodiment, the bend 45 defines an angle $\beta$ between the second section 39 and the probe tip 41 of approximately 111°–114°. The particular angle of the bend 45 is chosen so that, as best seen in FIG. 1, when the probe 31 and cannula 71 are assembled to form the drill guide 10, they are coaxial along the axis 12 within the smallest possible manufacturing tolerances.

With reference now to FIGS. 1 and 3, the slide 51 is seen to include a first end 53 and a second end 55 which is joined to the first end 53 via an intermediate section 54. The first end 53 of the slide 51 includes a slot 52 sized so as to fit over the outer periphery 16 of the first end 13 of the frame 11. The first end 53 of the slide 51 further includes a recess 56 which has inserted therein a spring member 57 having a flexible leg 58 which frictionally and resiliently engages the side 18 of the frame 11 so as to limit the ease with which the slide 51 slides over the surfaces 16 and 18 of the frame 11. If desired, the spring member 57 may extend throughout the length of the recess 56.

An adjusting means 60 is carried by the slide and enables the position of the slide 51 to be rigidly fixed with respect to the frame 11 at any location along the recess 15 of the frame 11. The adjusting means 60 consists of a nut 61 having elongated flat sides 62 and 63 which enable the nut 61 to be non-rotatably received within the recess 15 while allowing the nut 61 to freely reciprocate within the recess 15. The nut 61 includes internal threads 64 which cooperate with threads 66 carried on the stem portion 67 of a knob 65. The knob 65 includes a knob portion 68 and a neck 69 connecting the knob portion with the stem 67. As may best be seen in FIG. 3, the neck 69 has a reduced diameter with respect to the diameter of the stem 67 and this reduced diameter is provided for a particular purpose. In this regard, the slide 51 includes a bore 59 therethrough into which is inserted a pin 70. The bore 59 is provided in such a location that the pin 70 will be located closely adjacent the outer periphery of the neck 69 and with sufficient closeness thereto so as to prevent the stem 67 from being reciprocated therebeyond. Accordingly, the provision of the pin 70 prevents the adjusting means 60 from being inadvertantly or intentionally disassembled from the slide 51.

In a further aspect, the nut 61 includes a slot 61a through which the pin 70 is located for the purpose of limiting in and out (axial) movement of the nut 61 as it is threaded in either direction on the stem 67 of the knob 65. This pin-to-nut relationship precludes the possibility of the nut 61 from ever being totally unthreaded from knob 65 and thereby lost by falling out of slot 52. As should be understood from FIG. 3, when the slide 51 has been moved to a predetermined position with respect to the frame 11, and it is desired to lock the slide 51 and frame 11 into this predetermined configuration with respect to one another, the knob portion 68 is rotated so that the interaction between the threads 64 and 66 causes the surfaces 61b of the nut 61 to frictionally engage the surfaces 15a of the recess 15 to thereby, through frictional forces therebetween, lock the position of the slide 51 with respect to the frame 11.

As best seen with reference to FIG. 1, the intermediate portion 54 of the slide 51 includes a plurality of recesses 54a which enable the fingers of the surgeon to easily grip the slide 51 for sliding movements thereof.

Further, with particular reference to FIGS. 1 and 2, the second end 55 of the side 51 has integrally formed therewith a guide means 90 having angled ends 91 and 93 and a substantially cylindrical outer periphery 95. With particular reference to FIG. 2, the interior of the guide means 90 is defined by a first bore 97 and a second bore 98 of smaller diameter than the diameter of the first bore 97. The first and second bores 97 and 98 intersect with one another at a shoulder 99. Further, the walls defining the bore 98 include a recess 100 into which is installed an O-ring 101 for a purpose to be described hereinafter.

With reference now to FIGS. 1 and 2, it is seen that the cannula 71 includes a first end 73, a second end 75, and an intermediate portion 77. The first end 73 includes a terminus consisting of a multi-toothed face configuration 74 comprising a plurality of circumferentially spaced teeth 76. The first end 73 includes a substantially cylindrical outer wall portion 78. The intermediate portion 77 is connected to the first end 73 and includes a substantially cylindrical outer wall portion 80 of slightly greater diameter than the diameter of the surface 78 and which is connected to the surface 78 via a shoulder 81. It is noted that in the preferred embodiment there are five different cannulas in the system with through holes of 6, 7, 8, 9 and 10 millimeter diameter. The largest has no shoulder 81 because its outer wall 78 is continuous from shoulder 85 to the teeth at end 73.

The second end 75 includes a substantially cylindrical outer wall 83 that merges with the wall 80 via a further shoulder 85. At the terminus of the second end 75, a chamfered portion 87 is preferably provided. As best seen with reference to FIG. 2, a guide bore 88 extends completely through the cannula 71 and has a constant diameter and configuration throughout the length of the cannula from the first end 73 through the intermediate portion 77 to the second end 75. As best understood from FIGS. 1 and 2, the wall 83 of the cannula 71 conforms in outer diameter and configuration to the inner wall 98 of the guide means 90 so that the cannula 71 may be slidably inserted into the guide means 90 with the wall 83 slidably engaging the wall 98 and the O-ring 101 frictionally engaging the wall 83. As designed, the shoulder 85, in assembly of the cannula 71 to the guide means 90, positively engages the shoulder 99 of the guide means 90 with the wall 80 of the intermediate portion 77 of the cannula 71 slidably engaging the inner wall 97 of the guide means 90. When so assembled, as best seen in FIG. 1, the axes of the respective probe tip 41 and cannula 71, are maintained coaxial to as close a degree as possible in view of manufacturing tolerances.

The improved arthroscopic drill guide 10, having been described in detail hereinabove, its surgical use will now be described in detail.

As is well known, an arthroscopic surgical procedure may include the creation of a medial port, a mid-patellar port, a lateral port, or all three ports. The probe tip 41 of the inventive drill guide 10 may be inserted through the lateral port and seated at either the postero-medial face of the lateral femoral condyle or just forward of the intercondylar tibial spine, with this versatility being made possible by the bends 43 and 45 as explained hereinabove. Correct placement of the probe tip 41 may be monitored by the arthroscope through the medial or mid-patellar port and may be accordingly viewed on the associated television screen.

With such monitoring taking place, the slide 51 with the guide means 90 integrally formed therewith and the cannula 71 slidably mounted thereto may be then slid onto the frame 11 as best seen in FIGS. 1 and 3, adjusted to the appropriate axial position and locked into place through the use of the adjusting means 60. When so locked, the multi-toothed face configuration 74 of the cannula 71 should be biting into the facing bone so as to rigidly fix the position of the cannula 71 with respect thereto.

Because the inventive drill guide 10 is assembled with the terminus 49 of the probe tip 41 axially aligned with the axis of the cannula 71, the surgeon may easily drill through the cannula guide bore 88 (FIG. 2), egressing where the probe tip terminus 49 contacts the inside of the joint.

The design of the inventive drill guide is superior because the drill is guided through the cannula rather than over a pre-drilled wire as is the case with some prior art designs and as such the need for any preliminary pilot drilling or hit and miss guess work drilling is completely obviated thereby. The slidable adjustment of the slide 51 with respect to the frame 11 enables the inventive drill guide 10 to be used on many different sized bones in numerous applications. Again, and this cannot be stressed enough, the unique bends 43 and 45 of the probe 31 cause the inventive drill guide 10 to assume such a configuration that it is able to be utilized to drill the ligament tunnels in both the tibia and femur without the need for replacement of the probe 31.

The inventors have found the present invention to be extremely useful in reconstructing the anterior cruiciate ligament by facilitating its replacement with either synthetic ligaments or autogenous or allograft transplanted ligaments which are usually taken from the ipsilateral leg. Adaptability for posterior cruciate reconstruction is hypothesized.

In a further aspect, as explained hereinabove, the particular shape and configuration of the first and second sections 37 and 39 of the probe 31 are provided so as to prevent lateral bending of the probe 31 to thereby maintain the precise alignment of the tip 41 thereof with the axis of the cannula 71. These aspects of the probe 31 do not prevent the probe from flexing from left to right in the view of FIG. 1. Thus, as the slide 51 is reciprocated along the guide 15 of the frame 11 to a position where the multi-toothed face configuration 74 bites into the bone, the probe 31 may slightly flex in a spring-like manner in the left-hand direction of the view of FIG. 1. This slight flexure of the probe 31 facilitates the resilient gripping of the bone surfaces by the terminus 49 of the probe tip 41 and the teeth 76 of the multi-toothed face configuration 74 of the cannula 71. Such flexure enhances the retention of the drill guide 10, in assembled relation on the bone as desired and the flexure is so slight as to preclude any misalignment of the tip 41 with the axis of the cannula 71.

Accordingly, an invention has been disclosed hereinabove in terms of its structure and method of use which achieves all of the objectives set forth above and which constitutes a significant advance over the teachings of the prior art. In this light, it is noted that various changes, modifications and alterations in the teachings of the present invention may be contemplated by those skilled in the art without departing from the intended spirit and scope thereof. Accordingly, it is intended that the present invention only be limited by the terms of the following claims.

I claim:

1. An improved arthroscopic drill guide comprising:
   (a) a frame member;
   (b) a probe connected to one end of said frame member and including a first section adjacent said frame member, a second section connected to said first section, and a probe tip at an end of said second section remote from said first section, said probe tip extending along a longitudinal axis;
   (c) a slide member slidably connected to the other end of said frame member, said slide member including a guide at an end thereof remote from said frame member; and
   (d) a cannula slidably mounted to said guide, said cannula including a guide bore therethrough extending substantially along said longitudinal axis;
   (e) said probe member first section and second section having, substantially throughout their respective extents, cross sections elongated in a direction substantially perpendicular to said axis whereby said probe member is resistant to flexure forces which would tend to move said probe tip away from said axis to thereby maintain alignment of said probe tip and cannula along said axis.

2. The invention of claim 1, wherein said first section and second section intersect to form therebetween an obtuse angle chosen so that said drill guide may be utilized in drilling tunnels in both the proximal tibia and distal femur using a single probe member.

3. The invention of claim 2, wherein said obtuse angle is approximately 135°.

4. The invention of claim 2, wherein said second section and said probe tip intersect to form therebetween a further obtuse angle.

5. The invention of claim 4, wherein said further obtuse angle is about 111°–114°.

6. The invention of claim 1, wherein said frame member includes a hole into which said probe member first section is inserted, and said first section is soldered to said frame member.

7. The invention of claim 1, wherein said frame member other end includes a portion of C-shaped cross-section, said slide member including a corresponding portion of C-shaped cross-section slidably mounted over said frame member portion, said slide member further including adjusting means interacting with said frame member portion for controllably locking the position of said slide member with respect to said frame member.

8. The invention of claim 7, wherein said frame member portion defines a C-shaped recess, said adjusting means including:
(a) a nut slidably insertable into said C-shaped recess and having a threaded hole therethrough;
(b) a knob including a threaded stem threadably mounted in said threaded hole, said knob being rotatable in a first direction causing reciprocation of said nut means into frictional engagement with said C-shaped recess, and rotatable in a second direction releasing said frictional engagement.

9. The invention of claim 1, wherein said guide means includes an opening therethrough said cannula means being slidably inserted through said opening.

10. The invention of claim 9, wherein said opening defines a bore having a first bore section of a first diameter and a second bore section of a second diameter, said bore sections meeting at an internal annular shoulder, said cannula means having an outer annular shoulder adapted to abut, in assembly, said guide means internal annular shoulder.

11. The invention of claim 10, wherein one of said bore sections has mounted therein an O-ring protruding inwardly therefrom, said O-ring being adapted to frictionally engage said cannula means, in assembly.

12. The invention of claim 1, wherein said cannula means includes a face facing said probe tip, said face having a plurality of teeth formed therein.

* * * * *